(12) United States Patent
Alland et al.

(10) Patent No.: US 7,767,688 B2
(45) Date of Patent: Aug. 3, 2010

(54) COMBINATION OF PYRIMIDYLAMINOBENZAMIDE COMPOUNDS AND IMATINIB FOR TREATING GASTROINTESTINAL STROMAL TUMOURS

(75) Inventors: Leila Alland, Chatham, NJ (US); Paul W Manley, Arlesheim (CH); Juergen Mestan, Denzlingen (DE)

(73) Assignee: Novartis AG, Basel (CH)

( * ) Notice: Subject to any disclaimer, the term of this patent is extended or adjusted under 35 U.S.C. 154(b) by 41 days.

(21) Appl. No.: 11/915,650

(22) PCT Filed: Jun. 2, 2006

(86) PCT No.: PCT/US2006/021307

§ 371 (c)(1),
(2), (4) Date: Nov. 27, 2007

(87) PCT Pub. No.: WO2006/132930

PCT Pub. Date: Dec. 14, 2006

(65) Prior Publication Data

US 2008/0312252 A1    Dec. 18, 2008

Related U.S. Application Data

(60) Provisional application No. 60/687,758, filed on Jun. 3, 2005.

(51) Int. Cl.
*A61K 31/505* (2006.01)
(52) U.S. Cl. .................. 514/272; 514/252.14
(58) Field of Classification Search ............ 514/252.14, 514/272
See application file for complete search history.

(56) References Cited

FOREIGN PATENT DOCUMENTS

WO    WO 99/03854    1/1999
WO    WO 2004/005281    1/2004

OTHER PUBLICATIONS

Sausville et al. Cancer Research, 2006, vol. 66, pp. 3351-3354.*
Johnson et al. British J. of Cancer, 2001, 84(10):1424-1431.*
O'Hare et al. Cancer Cell, Feb. 2005, vol. 7, pp. 117-119.*
Sawyer et al. Curr. Med. Chem., 2004, vol. 4, No. 5, pp. 449-455.*
Hirota et al., "Pathology of gastrointestinal stromal tumors," Pathology International, vol. 56, pp. 1-9 (2006).
Druker et al., "Effects of a selective inhibitor of the Abl tyrosine kinase on the growth of Bcr-Abl positive cells," Nature Medicine, vol. 2, No. 5, pp. 561-566 (1996).
Heinrich et al., "Kinase Mutations and Imatinib Response in Patients with Metastatic Gastrointestinal Stromal Tumors," Journal of Clinical Oncology, vol. 21, No. 23, pp. 4342-4349 (2003).
Heinrich et al., "Biology and Genetic Aspects of Gastrointestinal Stromal Tumors: KIT Activation and Cytogenetic Alterations," Human Pathology, vol. 33, No. 5, pp. 484-495 (2002).
Heinrich et al., "PDGFRA Activation Mutations in Gastrointestinal Stromal Tumors," Science, vol. 299, pp. 708-710 (2003).
Corless et al., "PDGFRA Mutations in Gastrointestinal Stromal Tumors: Frequency, Spectrum and in Vitro Sensitivity to Imatinib," Journal of Clinical Oncology, vol. 23, No. 23, pp. 5357-5364 (2005).
Yi et al., "Epithelioid Gastrointestinal Stromal Tumor with PDGFRA Activation Mutation and Immunoreactivity," Applied Immunohistochemistry & Molecular Morphology, vol. 13, No. 2, pp. 157-161 (2005) Abstract only.
Weisberg et al., "Inhibition of mutant FLT3 receptors in leukemia cells by the small molecule tyrosine kinase inhibitor PKC412," Cancer Cell, vol. 1, pp. 433-443 (2002).
Weisberg et al., "Characterization of AMN107, a selective inhibitor of native and mutant Bcr-Abl," Cancer Cell, vol. 7, pp. 129-141 (2005).
Armstrong et al., "Inhibition of FLT3 in MLL: Validation of a therapeutic target identified by gene expression based classification," Cancer Cell, vol. 3, pp. 173-183 (2003).
Growney et al., "Activation mutations of human c-KIT resistant to imatinib mesylate are sensitive to the tyrosine kinase inhibitor PKC412," Blood, vol. 106, No. 2, pp. 721-724 (2005).
Gleixner et al., "PKC412 inhibits in vitro growth of neoplastic human mast cells expressing the D816V-mutated variant of KIT: comparison with AMN107, imatinib, and cladribine (2CdA) and evaluation of cooperative drug effects," Blood, vol. 107, No. 2, pp. 752-759 (2006).
Cools et al., "PKC412 overcomes resistance to imatinib in a murine model of FIP1L1-PDGFRα-induced myeloproliferative disease," vol. 3, pp. 459-469 (2003).
Cools, "The EOL-1 cell line as an in vitro model for the study of FIP1L1-PDGFRA-positive chronic eosinophilic leukemia," Blood, vol. 103, No. 7, pp. 2802-2805, (2004).
Le Coutre et al., "Activity and Induction of Apoptosis of the Specific Tyrosine Kinase Inhibitor AMN 107 in bcr-abl + Cell Lines and in Imatinib Resistant Primary Cells from CML Patients," Blood, vol. 104:218a; (2004) Abstract only.
Demetri et al., "Efficacy and safety of imatinib mesylate in advanced gastrointestinal stromal tumors," New England Journal of Medicine, vol. 347, No. 7, pp. 472-480 (2002).
Ohashi et al., "Different Inhibitory Effect of Imatinib on Phosphorylation of Mitogen-Activated Protein Kinase and AKT and on Proliferation in Cells Expressing Different Types of Mutant Platelet-Derived Growth Factor Receptor," Int. J. Cancer, vol. 111, pp. 317-321 (2004).
Fabbro et al., "PKC412—a protein kinase inhibitor with a broad therapeutic potential," Anticancer Drug Des., vol. 15, pp. 17-28 (2000).
Debiec-Rychter et al., "Mechanisms of Resistance to Imatinib Mesylate in Gastrointestinal Stromal Tumors and Activity of the PKC412 Inhibitor Against Imatinib-Resistant Mutants," Gastroenterology, vol. 128, pp. 270-279 (2005).
Prenen et al., "Cellular Uptake of the Tyrosine Kinase Inhibitors Imatinib and AMN107 in Gastrointestinal Stromal Tumor Cell Lines," Pharmacology, vol. 77, pp. 11-16 (2006).

(Continued)

*Primary Examiner*—James D Anderson
(74) *Attorney, Agent, or Firm*—Sandra Shim

(57) ABSTRACT

The invention provides a pharmaceutical combination comprising:
  a) a pyrimidylaminobenzamide compound, and
  b) imatinib.
and a method for treating or preventing a proliferative disease, especially GIST, using such a combination.

1 Claim, No Drawings

OTHER PUBLICATIONS

White et al. "OCT-1-mediated influx is a key determinant of the intracellular uptake of Imatinib but not nilotinib (AMN107): reduced OCT-1 activity is the cause of low in vitro sensitivity to Imatinib," Blood, vol. 108, No. 2, pp. 697-704 (2006).

Demetri George D., et al: "A phase I study of signle-agent nilotinib or in combination with imatinib in patients with imatinib-resistant gastrointestinal stromal tumors", Clinical Cancer Research, vol. 15, No. 18, pp. 5910-5916, Sep. 15, 2009.

Weisberg Ellen, et al: "Effects of PKC412, nilotinib, and imatinib against GIST-associated PDGFRA mutants with differential imatinib sensitivity", Gastroenterology 2006 vol. 131, pp. 1734-1742.

* cited by examiner

COMBINATION OF PYRIMIDYLAMINOBENZAMIDE COMPOUNDS AND IMATINIB FOR TREATING GASTROINTESTINAL STROMAL TUMOURS

This application claims benefit of U.S. Provisional Application No. 60/687,758, filed Jun. 3, 2005.

The present invention relates to a pharmaceutical combination comprising a (a) pyrimidylaminobenzamide derivative compound and (b) 4-(4-methylpiperazin-1-ylmethyl)-N-[4-methyl-3-(4-pyridin-3-yl)pyrimidin-2-ylamino)phenyl]-benzamide (Imatinib which is sold under the name Gleevec®), and the uses of such a combination for the treatment of, proliferative diseases, most preferably gastrointestinal stromal tumours (GIST).

Gastrointestinal stromal tumours (GISTs) are a recently characterized family of mesenchymal neoplasms, which originate from the gastrointestinal tract, most commonly from the stomach (60 to 70% of all GISTs). In the past, these tumours were variously classified as leiomyoma, leiomyoblastoma, or leiomyosarcoma. However, it is now clear that GISTs represent a distinct clinicopathologic set of diseases based on their unique molecular pathogenesis and clinical features. GISTs occur most commonly in the middle-aged or elderly with a median age of 50 to 60 years at presentation, and show no significant sex difference in the incidence. It is estimated that at least 10-30% of GISTs are malignant giving rise to intra-abdominal spread and metastases, which are most commonly found in the liver and peritoneal seeding. Malignant GISTs occur at an annual frequency of about 0.3 new cases per 100.000. The most common presenting symptom is vague upper abdominal pain. Many (30%) are asymptomatic, and GISTs may be diagnosed during the evaluation of anaemia resulting from tumour-associated gastrointestinal bleeding.

Management of metastatic and inoperable GIST is a major problem, since GISTs are notoriously unresponsive to cancer chemotherapy. For example, in one recent phase II series, 12 out of 18 (67%) patients with advanced leiomyosarcomas responded to a regimen consisting of dacarbazine, mitomycin, doxorubicin, cisplatin, and sargramostim, but only one (5%) out of 21 GISTs responded (J. Edmonson, R. Marks, J. Buckner, M. Mahoney, Proc. Am. Soc. Clin. Oncol. 1999; 18: 541a "Contrast of response to D-MAP+sargramostin between patients with advanced malignant gastrointestinal stromal tumors and patients with other advanced leiomyosarcomas"). Treatment results have remained equally unimpressive with other chemotherapy regimens. In line with clinical chemoresistance, expression of P-glycoprotein and muitidrug resistance protein MRP1 that associate with multidrug resistance (MDR) are more pronounced in malignant GISTs as compared with leiomyosarcomas.

In spite of numerous treatment options for proliferative disease patients, there remains a need for effective and safe antiproliferative agents and a need for their preferential use in combination therapy.

It has now surprisingly been demonstrated that GIST can be successfully treated with pyrimidylaminobenzamide derivatives or pharmaceutically acceptable salts thereof, alone or in combination with Imatinib.

SUMMARY OF THE INVENTION

It has now been found that a combination comprising (a) at least one pyrimidylaminobenzamide compound and (b) imatinib, e.g. as defined below, has a beneficial effect on proliferative diseases, e.g. tumors, and most especially GIST.

DETAILED DESCRIPTION OF THE INVENTION

The present invention relates to the use of pyrimidylaminobenzamide compounds of formula (I):

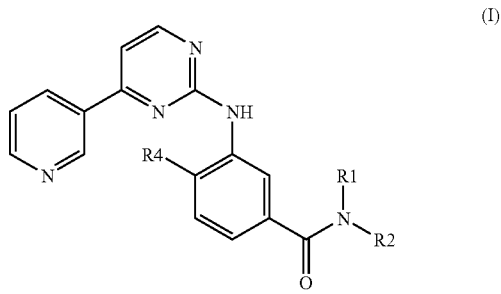

wherein $R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

and a N-oxide or a pharmaceutically acceptable salt of such a compound for the preparation of a pharmaceutical composition for the treatment of kinase dependent diseases.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)$_2$), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substituents selected from the group defined above as substituents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substituents selected from the group defined above as substituents for aryl, most preferably by lower alkyl, such as methyl, lower alkoxy, such as methoxy or ethoxy, or hydroxy. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)-2-one. In another preferred embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Compounds within the scope of formula (I) and the process for their manufacture are disclosed in WO 04/005281 published on Jan. 15, 2004 which is hereby incorporated into the present application by reference. A preferred compound is 4-Methyl-3-[[4-(3-pyridinyl)-2-pyrimidinyl]amino]-N-[5-(4-methyl-1H-imidazol-1-yl)-3-(trifluoromethyl)phenyl]benzamide, and pharmaceutically acceptable salts thereof, of the formula (II):

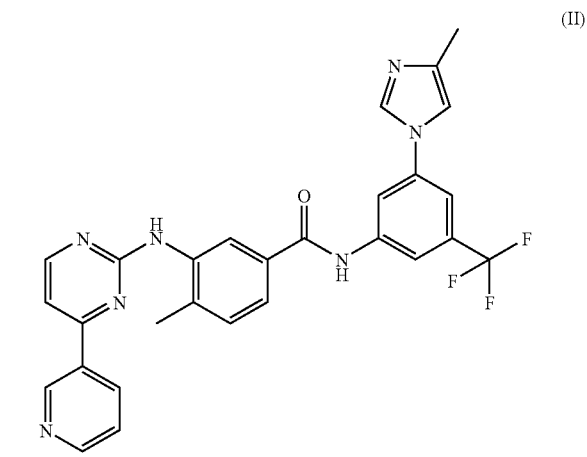

Combinations of the present invention include the compound 4-(4-methylpiperazin-1-ylmethyl)-N-[4-methyl-3-(4- pyridin-3-yl)pyrimidin-2-ylamino)phenyl]-benzamide (Imatinib which is sold under the name Gleevec®) is of the formula (III):

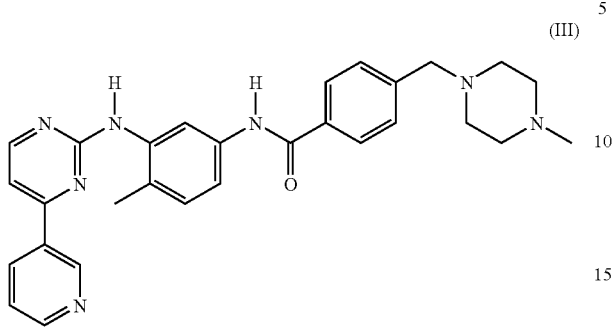

The preparation of Compound (III) and the use thereof, especially as an anti-tumour agent, are described in Example 21 of European patent application EP-A-0 564 409, which was published on 6 Oct. 1993, and in equivalent applications and patents in numerous other countries, e.g. in U.S. Pat. No. 5,521,184 and in Japanese patent 2706682.

The monomethanesulfonic acid addition salt of Compound (III) and a preferred crystal form thereof are described in PCT patent application WO99/03854 published on Jan. 28, 1999.

Comprised are likewise the pharmaceutically acceptable salts thereof, the corresponding racemates, diastereoisomers, enantiomers, tautomers, as well as the corresponding crystal modifications of above disclosed compounds where present, e.g. solvates, hydrates and polymorphs, which are disclosed therein. The compounds used as active ingredients in the combinations of the invention can be prepared and administered as described in the cited documents, respectively. Also within the scope of this invention is the combination of more than two separate active ingredients as set forth above, i.e., a pharmaceutical combination within the scope of this invention could include three active ingredients or more.

In accordance with the particular findings of the present invention, there is provided
1. A pharmaceutical combination comprising:
   a) a pyrimidylaminobenzamide compound of formula (I); and
   b) imatinib of formula (III).
2. A method for treating or preventing proliferative disease in a subject in need thereof, comprising co-administration to said subject, e.g., concomitantly or in sequence, of a therapeutically effective amount of a pyrimidylaminobenzamide compound of formula (I) and imatinib of formula (III), e.g., as disclosed above.
Examples of proliferative diseases include e.g. tumors, most especially preferred is GIST.
3. A pharmaceutical combination as defined under 1) above, e.g. for use in a method as defined under 2) above.
4. A pharmaceutical combination as defined under 1) above for use in the preparation of a medicament for use in a method as defined under 2) above.
5. A pharmaceutical combination comprising:
   a) preferably, a compound of formula (II); and
   b) imatinib of formula (III).
6. A method for treating or preventing proliferative disease in a subject in need thereof, comprising co-administration to said subject, e.g., concomitantly or in sequence, of a therapeutically effective amount of a compound of formula (I) and imatinib of formula (III), e.g., as disclosed above.
7. A pharmaceutical combination as defined under 5) above, e.g. for use in a method as defined under 6) above.
8. A pharmaceutical combination as defined under 5) above for use in the preparation of a medicament for use in a method as defined under 7) above.
Utility of the combination of the invention in a method as hereinabove specified, may be demonstrated in animal test methods as well as in clinic, for example in accordance with the methods hereinafter described.

A. Combined Treatment

Suitable clinical studies are, for example, open label, dose escalation studies in patients with proliferative diseases, especially GIST. Such studies prove in particular the synergism of the active ingredients of the combination of the invention. The beneficial effects on GIST can be determined directly through the results of these studies which are known as such to a person skilled in the art. Such studies are, in particular, suitable to compare the effects of a monotherapy using the active ingredients and a combination of the invention. Preferably, the dose of agent (a), e.g. compound (I) or preferably compound (II), is escalated until the Maximum Tolerated Dosage is reached, and agent (b) is administered with a fixed dose. Alternatively, the agent (a) is administered in a fixed dose and the dose of agent (b) is escalated. Each patient receives doses of the agent (a) either daily or intermittent. The efficacy of the treatment can be determined in such studies, e.g., after 12, 18 or 24 weeks by evaluation of symptom scores every 6 weeks.

The administration of a pharmaceutical combination of the invention results not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit is that lower doses of the active ingredients of the combination of the invention can be used, for example, that the dosages need not only often be smaller but are also applied less frequently, which may diminish the incidence or severity of side-effects. This is in accordance with the desires and requirements of the patients to be treated.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

It is one objective of this invention to provide a pharmaceutical composition comprising a quantity of a combination of the invention, which is jointly therapeutically effective at targeting or preventing proliferative diseases, especially GIST. In this composition, agent (a) and agent (b) may be administered together, one after the other or separately in one combined unit dosage form or in two separate unit dosage forms. The unit dosage form may also be a fixed combination.

The pharmaceutical compositions for separate administration of agent (a) and agent (b) or for the administration in a fixed combination, i.e. a single galenical composition comprising at least two combination partners (a) and (b), according to the invention may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

Suitable pharmaceutical compositions contain, for example, from about 0.1% to about 99.9%, preferably from about 1% to about 60%, of the active ingredient(s). Pharmaceutical preparations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partner of the combination of the invention may be administered simultaneously or sequentially and in any order, and the components may be administered separately or as a fixed combination. For example, the method of preventing or treating proliferative diseases according to the invention may comprise (i) administration of the first agent (a) in free or pharmaceutically acceptable salt form and (ii) administration of an agent (b) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition. Optimal precision in achieving concentration of the active ingredients within the range that yields efficacy without toxicity requires a regimen based on the kinetics of the active ingredients' availability to target sites.

Daily dosages for agent (a) or (b) or will, of course, vary depending on a variety of factors, for example the compound chosen, the particular condition to be treated and the desired effect.

Preferably the compound of formula (I), agent (a) is administered orally, preferably at a daily dosage of 1-300 mg/kg body weight or, for most larger primates, a daily dosage of 50-5000, preferably 500-3000 mg. A preferred oral daily dosage is 1-75 mg/kg body weight or, for most larger primates, a daily dosage of 10-2000 mg, administered as a single dose or divided into multiple doses, such as twice daily dosing.

Agent (b) may be administered to a human in a daily dosage range of 0.5 to 1000 mg. Suitable unit dosage forms for oral administration comprise from ca. 0.1 to 500 mg active ingredient, together with one or more pharmaceutically acceptable diluents or carriers therefore.

In general, however, satisfactory results are achieved on administration of agent (b) at daily dosage rates of the order of ca. 0.03 to 5 mg/kg per day, particularly 0.1 to 5 mg/kg per day, e.g. 0.1 to 2.5 mg/kg per day, as a single dose or in divided doses. Agent (a) and agent (b) may be administered by any conventional route, in particular enterally, e.g. orally, e.g. in the form of tablets, capsules, drink solutions or parenterally, e.g. in the form of injectable solutions or suspensions, together with one or more pharmaceutically acceptable diluents or carriers therefore.

The administration of a pharmaceutical combination of the invention results not only in a beneficial effect, e.g. a synergistic therapeutic effect, e.g. with regard to inhibiting the unregulated proliferation of, or slowing down the progression of the growth of tumors, but also in further surprising beneficial effects, e.g. less side-effects, an improved quality of life or a decreased morbidity, compared to a monotherapy applying only one of the pharmaceutically active ingredients used in the combination of the invention.

A further benefit is that lower doses of the active ingredients of the combination of the invention can be used, for example, that the dosages need not only often be smaller but are also applied less frequently, or can be used in order to diminish the incidence of side-effects. This is in accordance with the desires and requirements of the patients to be treated.

B. Diseases to be Treated

The term "proliferative disease" includes but is not restricted to tumors, psoriasis, restenosis, sclerodermitis and fibrosis.

The term haematological malignancy, refers in particular to leukemias, especially those expressing Bcr-Abl, c-Kit or Flt-3, and includes, but is not limited to, chronic myelogenous leukemia and acute lymphocyte leukemia (ALL), especially the Philadelphia chromosome positive acute lymphocyte leukemia (Ph+ALL) as well as STI571-resistant leukemia.

The term "a solid tumor disease" especially means ovarian cancer, breast cancer, cancer of the colon and generally the gastrointestinal tract, cervix cancer, lung cancer, e.g. small-cell lung cancer and non-small-cell lung cancer, head and neck cancer, bladder cancer, cancer of the prostate or Kaposi's sarcoma.

The combinations according to the invention, that inhibit the protein kinase activities mentioned, especially tyrosine protein kinases mentioned above and below, can therefore be used in the treatment of protein kinase dependent diseases. Protein kinase dependent diseases are especially proliferative diseases, preferably benign or especially malignant tumours (for example carcinoma of the kidneys, liver, adrenal glands, bladder, breast, stomach, ovaries, colon, rectum, prostate, pancreas, lungs, vagina or thyroid, sarcoma, glioblastomas and numerous tumours of the neck and head, as well as leukemias). They are able to bring about the regression of tumours and to prevent the formation of tumour meta-stases and the growth of (also micro)metastases. In addition they can be used in epidermal hyperproliferation (e.g. psoriasis), in prostate hyperplasia, and in the treatment of neo-plasias, especially of epithelial character, for example mammary carcinoma. It is also possible to use the combinations of the present invention in the treatment of diseases of the immune system insofar as several or, especially, individual tyrosine protein kinases are involved; furthermore, the combinations of the present invention can be used also in the treatment of diseases of the central or peripheral nervous system where signal transmission by at least one tyrosine protein kinase, especially selected from those mentioned specifically, is involved.

In chronic myelogeous leukemia (CML), a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyro-sine kinase, which plays a fundamental role in regulating cell proliferation, adherence and apoptosis, the BCR-ABL fusion gene encodes as constitutively activated kinase, which trans-forms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. The resulting granulocytes fail to develop into mature lymphocytes and are released into the circulation, leading to a deficiency in the mature cells and increased susceptibility to infection. ATP-competitive inhibitors of Bcr-Abl have been described which prevent the kinase from activating mitogenic and anti-apoptotic pathways (e.g. P-3 kinase and STAT5), leading to the death of the BCR-ABL phenotype cells and thereby providing an effective therapy against CML. The combinations of the present invention are thus especially appropriate for the therapy of diseases related to its overexpression, especially leukemias, such as leukemias, e.g. CML or ALL.

The combinations of the present invention primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases (solid tumors, but also leukemias and other haematological malignancies), such as especially breast cancer, cancer of the colon, lung cancer (especially small-cell lung cancer), cancer of the prostate or Kaposi's sarcoma. Combinations of the present invention inhibit the growth of tumours and are especially suited to preventing the metastatic spread of tumors and the growth of micrometastases.

The invention relates to a method of treating myeloma, especially myeloma which is resistant to conventional chemotherapy. The term "myeloma" as used herein relates to a tumor composed of cells of the type normally found in the bone marrow. The term "multiple myeloma" as used herein means a disseminated malignant neoplasm of plasma cells which is characterized by multiple bone marrow tumor foci and secretion of an M component (a monoclonal immunoglobulin fragment), associated with widespread osteolytic lesions resulting in bone pain, pathologic fractures, hypercalcaemia and normochromic normocytic anaemia. Multiple myeloma is incurable by the use of conventional and high dose chemotherapies. The invention relates to a method of treating myeloma, especially myeloma which is resistant to conventional chemotherapy.

EXAMPLE

Activating mutations in platelet-derived growth factor receptor alpha (PDGFRA) have been reported in a subset of gastrointestinal stromal tumor (GIST) patients who do not express mutant stem cell factor receptor, c-KIT. The responsiveness of mutant PDGFRA-positive GIST to imatinib depends on the location of the PDGFRA mutation: for example the V561D juxtamembrane domain mutation, is more sensitive to imatinib than the D842V kinase domain mutation. In this example, the effects of Compound (II) and imatinib [Compound (III)] on two GIST-related PDGFRA mutants, V561D and D842V, which possess differential sensitivity to imatinib, are investigated.

Cell lines and cell culture: Constructs of D842V-, V561D- and wild-type (wt)-PDGFRA cDNA cloned into pcDNA3.1 (obtained from M. C. Heinrich, Oregon Health & Science University Cancer Institute, Portland, Oreg.) are stably transfected into Ba/F3 cells by electroporation, and cells are selected for neomycin resistance and IL3-independent growth. All cells are cultured in the presence of 5% $CO_2$ at 37° C., at a concentration of $5 \times 10^5$ cells/mL, in cellgro RPMI 1640 medium (Mediatech, Inc. Herndon, Va.), supplemented with 10% fetal calf serum (FCS; Harlan Bioproducts, Indianapolis, Ind.), 1% glutamine, and penicillin/streptomycin. Parental Ba/F3 cells or wt-PDGFRA-Ba/F3 cells are cultured with 15% WEHI-conditioned medium as a source of IL-3. All transfected cells are cultured in media supplemented with 1 mg/mL G418.

Antibodies and Immunoblotting: Anti p-Tyr (clone 4G10, Upstate Biotechnology, NY) is used at 1:1000 for immunoblotting. PDGFRA antibody (C-20, Santa Cruz Biotechnology, CA) is used at 1:200 for immunoblotting. Protein lysis preparation and immunoblotting are carried out as previously described. Weisberg et al., Cancer Cell 2002; 1: 433-443.

Proliferation studies: The trypan blue exclusion assay has been previously described (Weisberg et al., Cancer Cell 2002; 1: 433-443) and is used for all cell proliferation studies. Compound II and imatinib are added simultaneously at fixed ratios to either D842V- or V561D-PDGFRA-Ba/F3 cells. Dose-response curves are generated and combination indices are calculated as described in Weisberg et al., Cancer Cell 2005; 7:129-141.

Mouse studies and in vivo imaging: D842V-PDGFRA-Ba/F3 cells are transduced with a retrovirus encoding firefly luciferase (MSCV-Luc), and selected with puromycin at a concentration of 0.5 µg/mL to generate the D842V-PDGFRA-Ba/F3-luciferase (luc+) cell line. Cells free of Mycoplasma and viral contamination are resuspended in Hank's Balanced Salt Solution (HBSS; Mediatech, Inc., VA) prior to i.v. administration to mice. Solutions of Compound II are prepared by dissolving 200 mg in 1.0 mL of NMP to give a clear solution, and are diluted daily prior to administration with 9.0 mL PEG300. Placebo mice received vehicles for Compound II are administered 30-45 minutes apart.

Male NCR-nude mice (5-6 weeks of age; Taconic, N.Y.) are administered a total of 600,000 D842V-PDGFRA-Ba/F3-luc+ cells by tail vein injection. Mice are imaged and total body luminescence quantified as previously described (Armstrong et al., Cancer Cell 2003; 3:173-183). Baseline imaging one day after tumor cell inoculation is used to establish treatment cohorts with matched tumor burden. Cohorts of mice are treated with oral administration of vehicle, 150 mg/kg/day Compound II (formulated as above; 6 days total treatment). Repeat imaging is performed at various intervals.

Combination effects of Compound II and imatinib: D842V-PDGFRA-Ba/F3:

Combinations of Compound II and imatinib are tested against D842V-PDGFRA-Ba/F3 cells. Overall, positive combination effects are observed between Compound II plus imatinib. Calcusyn analysis of the combined effects of Compound II plus imatinib suggests synergistic to nearly additive effects across a range of doses (ED25-ED75), with antagonism at ED90 (Table I).

Combination effects of Compound II with imatinib: V561D:

The effects of combinations of Compound II with imatinib are evaluated against V561D-PDGFRA-Ba/F3. Generally, both combinations led to varying degrees of antagonism across a range of doses in the V561D-PDGFRA-Ba/F3 cell line (Table I).

TABLE 1

Combination Indices Calculated From Dose-response Curves

| Cell Line (Treatments) | ED25 | ED50 | ED75 | ED90 |
|---|---|---|---|---|
| D842V-Ba/F3 (Compound II + imatinib) | 0.48812 | 0.73221 | 1.09836 | 1.64762 |
| V561D-Ba/F3 (Compound II + imatinib) | 0.80100 | 1.00712 | 1.81556 | 5.23012 |

We claim:

1. A method for treating gastrointestinal stromal tumours comprising administering to a subject in need of treatment of gastrointestinal stromal tumors a pharmaceutical combination comprising a) 4-Methyl-3-[[4-(3-pyridinyl)-2-pyrimidinyl]amino]-N-[5-(4-methyl-1H-imidazol-1-yl)-3-(trifluoromethyl)phenyl]benzamide, of the formula (II):

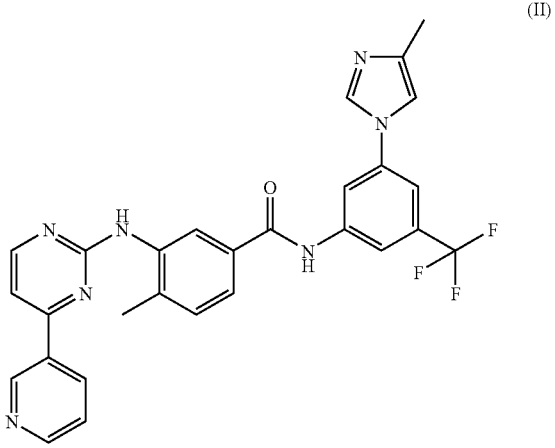

or a pharmaceutically acceptable salt thereof,
and
b) imatinib.

* * * * *